United States Patent [19]

Brown

[11] 4,298,750
[45] Nov. 3, 1981

[54] BORANE-1,4-THIOXANE

[75] Inventor: Herbert C. Brown, West Lafayette, Ind.

[73] Assignee: Aldrich-Boranes, Inc., Milwaukee, Wis.

[21] Appl. No.: 122,285

[22] Filed: Feb. 19, 1980

[51] Int. Cl.$^3$ ............................................. C07D 327/06
[52] U.S. Cl. .................................... 549/4; 260/346.11; 568/6; 568/7; 568/814; 568/837; 568/838; 568/885
[58] Field of Search ............................................ 549/4

[56] References Cited
U.S. PATENT DOCUMENTS
3,314,990  4/1967  Miller .................................. 549/4 X

OTHER PUBLICATIONS

Baker et al., Chemical Abstracts, vol. 68, abst. No. 101,333v (1968).
Lowey et al., An Introduction to Organic Chemistry, 6th Ed., p. 214, John Wiley & Sons, Inc. NY (1945).

Primary Examiner—John D. Randolph
Attorney, Agent, or Firm—Merriam, Marshall & Bicknell

[57] ABSTRACT

The novel borane-1,4-thioxane is synthesized by adding the calculated quantity of diborane to 1,4-thioxane. It is a stable liquid at 25° C. The neat liquid is approximately 8.0 M in borane. The product, in spite of the additional oxygen atom in the ring, exhibits the desirable hydroborating and reducing action of borane-methyl sulfide. However, it possesses a major advantage over the latter in that the donor component, 1,4-thioxane, in contrast to methyl sulfide, is readily soluble in water and can be washed out of typical reaction mixtures. This greatly facilitates the synthetic applications of borane-1,4-thioxane over borane-methyl sulfide.

4 Claims, No Drawings

BORANE-1,4-THIOXANE

This invention relates to borane derivatives, their methods of production and their use in the hydroboration and reduction of organic compounds. More particularly, this invention provides the novel borane-1,4-thioxane, a method of producing it and hydroboration and reduction processes using it.

Prior Art

Borane-tetrahydrofuran is a valuable reagent for the hydroboration of olefins and for the reduction of organic compounds. The following reactions are representative:

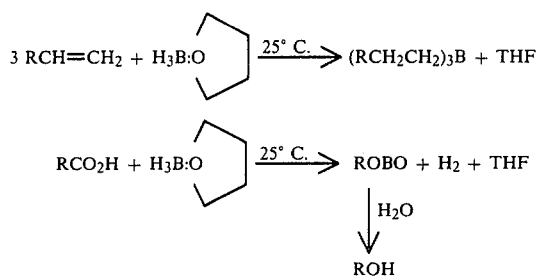

wherein R represents an organic group and THF is an abbreviation for tetrahydrofuran. It suffers from the disadvantage in that the solutions are unstable over a period of time [J. Kollonitsch, J. Am. Chem. Soc., 83, 1515 (1961)].

Borane-methyl sulfide (BMS) is much more stable and is widely used for both hydroboration and reduction [Burg et al, J. Am. Chem. Soc. 76, 3307 (1954) and Coyle et al, J. Am. Chem. Soc. 81, 2989 (1959)]. However, it suffers from a serious disadvantage in that it yields a product which contains free dimethyl sulfide, as shown by the following typical reactions:

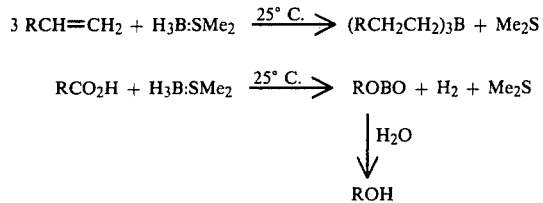

wherein R represents an organic group.

The free dimethyl sulfide is highly volatile, b.p. 35° C., and has a very noxious odor. Moreover, it is not soluble in water, so it cannot be disposed of by washing it away with water.

BACKGROUND OF THE INVENTION

A purpose of this invention is to provide a stable hydroborating and reducing agent in which the donor residue can be washed away with water.

One possibility considered was the use of amines as the donor molecule. However, the amine-borane derivatives examined are too stable to permit hydroboration and reduction under mild conditions, such as represented by the following reaction:

$3RCH=CH_2 + H_3B:NEt_3 \xrightarrow{25° \text{ C.}}$ No reaction wherein R represents an organic group and Et represents ethyl.

It appeared that the disadvantage of tetrahydrofuran might be solved by using dioxane. The 6-membered ring in dioxane is less readily ruptured than the 5-membered ring in tetrahydrofuran. However, diborane does not dissolve in dioxane in the manner in which it dissolves in tetrahydrofuran to form an addition compound. This can be illustrated as follows:

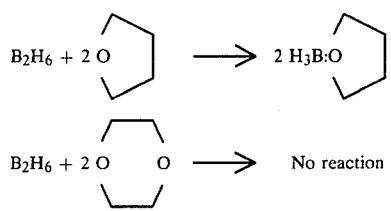

Evidently the presence of the second oxygen atom in the dioxane ring weakens the donor properties of the first oxygen atom so that coordination with borane, sufficiently strong so as to dissociate the diborane dimer, does not occur.

The above result made it improbable that 1,4-thioxane having the formula:

would serve to solve the problem. This compound also contains an oxygen atom which should operate to diminish the donor properties of the sulfur atom. Indeed, no one has ever reported examining the behavior of 1,4-thioxane toward diborane.

According to the invention, it has been discovered that diborane is readily soluble in 1,4-thioxane. Moreover, diborane added until the solution is saturated yields the novel borane addition compound, borane-1,4-thioxane as shown by the following reaction:

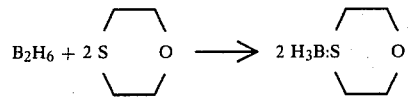

This novel product is a stable liquid at room temperature and is 8.0 M in borane. On cooling, it solidifies, m.p. 11°–15° C.

Borane-1,4-thioxane is an excellent hydroborating and reducing agent, which is miscible with the standard solvents utilized for hydroboration, i.e. tetrahydrofuran, ethyl ether and methylene chloride, and it is partially soluble in pentane. It performs all of the functions achieved by borane-methyl sulfide.

1,4-Thioxane is much less volatile than dimethyl sulfide and its odor is far less unpleasant. Consequently, borane-1,4-thioxane is far easier to work with than borane-methyl sulfide. Even more important, 1,4-thioxane possesses a modest solubility in water (0.3 M). Consequently, it is a simple matter to remove the donor residue from the product in a solvent, such as diethyl ether, methylene chloride or pentane, merely by washing it with water.

Borane-1,4-thioxane hydroborates essentially all olefins rapidly and quantitatively, desirably in an inert liquid reaction medium, to yield a wide variety of fully or partially substituted organoboranes. Thus, it hydroborates alkenes rapidly to form the corresponding trialkylboranes in excellent yields. This reaction can be represented as follows:

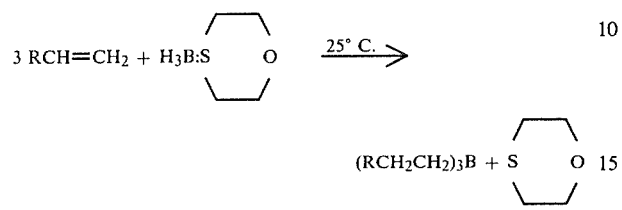

wherein R signifies an organic group, and particularly a hydrocarbon group. The reaction product can be oxidized with alkaline hydrogen peroxide to provide an alcohol in essentially quantitative yield. Alternatively, the reaction mixture can be treated with aqueous sodium hypochlorite to selectively oxidize the 1,4-thioxane component to the sulfoxide without oxidizing the organoborane component. The sulfoxide is highly soluble in water and can be readily extracted into the aqueous phase. The residual organoborane in the organic phase then can be recovered, dried, and utilized for the many transformations that organoboranes undergo, as see Brown et al, Organic Syntheses via Boranes, Wiley-Interscience, New York, N.Y., 1975.

Borane-1,4-thioxane is useful in the reduction of organic compounds. Thus, it can be used to reduce carboxylic acids to alcohols according to the following procedure:

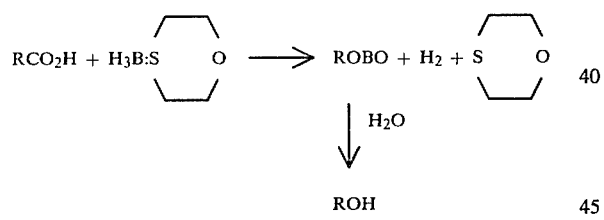

wherein R represents an organic group, especially a hydrocarbon group which, for example, can be an alkyl, cycloalkyl, aryl or aralkyl group.

The hydroboration-oxidation reaction with borane-1,4-thioxane exhibits the same high regio- and stereoselectivity of the earlier borane reagents used for this purpose. The following reaction illustrates such a reaction.

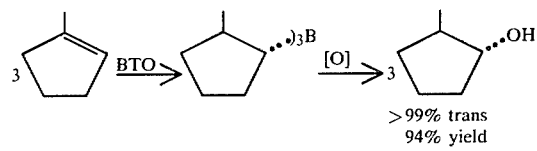

Functional groups which can be reduced by hydroboration with borane-1,4-thioxane followed by hydrolysis can be summarized as follows: aldehydes to alcohols; ketones to alcohols; lactones to glycols; amides to amines; epoxides to alcohols; esters to alcohols; carboxylic acids to alcohols; and nitriles to amines. The reaction is achieved using an effective quantity of borane-1,4-thioxane at a temperature below the decomposition temperature of the reactants or the resulting product.

The following examples are presented to further illustrate the invention.

EXAMPLE 1

Preparation of Borane-1,4-Thioxane

All operations were carried out under nitrogen. Diborane gas was generated by reacting sodium borohydride (21.6 g, 550 mmol) in diglyme (145 ml) with boron trifluoride etherate (91.2 ml, 724 mmol) and passing the gas evolved into 1,4-thioxane (56.2 ml, 540 mmol) at room temperature (25° C.) to saturation. Excess diborane was passed into dry tetrahydrofuran (THF). An aliquot of the borane-1,4-thioxane neat reagent thus formed was analyzed by hydrolysis. The hydrogen evolved corresponded to a concentration of 8.0 M in borane. On cooling the product to 0° C., it crystallized and these crystals melted at 11°–15° C. Its $^{11}$B NMR spectrum exhibits only one absorption at $-23.0\delta$ (relative to $BF_3.OEt_2$), supporting formation of the borane-1,4-thioxane complex by coordination of borane with the sulfur atom (BMS: $-20.3\delta$; $BH_3$-THF $+1.0\delta$). The neat reagent is stable at 25° C. for long periods of time, without exhibiting detectable change in the hydride content or in the $^{11}$B spectrum.

EXAMPLE 2

Hydroboration of 1-hexene with borane-1,4-thioxane was examined in tetrahydrofuran, ethyl ether, methylene chloride and pentane. All reactions were at room temperature (25° C.) and involved the addition of 1-hexene (15 mmol) to borane-1,4-thioxane (5 mmol) in sufficient solvent to make the reaction mixture 0.75 M in borane.

Five minutes after completion of the hydroboration, the products were oxidized by alkaline hydrogen peroxide and the alcohols formed determined by gas chromatography. The results are summarized in Table 1.

TABLE 1

| Solvent | 1-Hexanol,[a]% | 2-Hexanol,[a]% | Total Yield,[b]% |
|---|---|---|---|
| Tetrahydrofuran | 94 | 6.0 | 99.3 |
| Diethyl ether[c] | 93.5 | 6.5 | 94.0 |
| Pentane[c] | 93.0 | 7.0 | 100 |
| Methylene chloride[c] | 93.0 | 7.0 | 100 |

[a]Relative amounts by gas chromatography (GC) analysis.
[b]Total yield by GC using an internal standard.
[c]Ethanol (3.0 ml) was added prior to oxidation.

EXAMPLE 3

Representative alkenes were treated with borane-1,4-thioxane, in a ratio of 3 mols of alkene to 1 mol of the reagent, in tetrahydrofuran (0.75 M in borane) under the conditions reported in Table 2. Following completion of the hydroboration, the products were oxidized by alkaline hydrogen peroxide. The resulting alcohol yields are given in Table 2.

The data in Table 2 indicates that the hydroboration proceeds smoothly. Oxidation of the organoborane produced in the hydroboration stage afforded excellent yields of the corresponding alcohols. Just as in the case of BMS, the reaction of borane-1,4-thioxane with most of the alkenes examined is so fast at 25° C. that the rate of hydroboration could not be followed. However, the reaction with cyclohexene is relatively slow. Consequently, the rate of hydroboration with borane-1,4-thioxane and with borane-methyl sulfide (BMS) was followed to compare the relative reactivities of the two reagents. The results reveal that borane-1,4-thioxane reacts at a significantly faster rate than BMS.

TABLE 2

| Alkene | Time min. | Alcohol Products | Relative amounts,[a]% | Total Yield,[b]% |
| --- | --- | --- | --- | --- |
| 1-Hexene | 5[c] | 1-Hexanol | 94.0 | 99.3 |
|  |  | 2-Hexanol | 6.0 |  |
| 1-Octene | 5[c] | 1-Octanol | 93.4 | 93.9(84)[d] |
|  |  | 2-Octanol | 6.6 |  |
| Styrene | 5[c] | 2-Phenyl-ethanol | 84.6 | 96.0 |
|  |  | 1-phenyl-ethanol | 15.4 |  |
| 2-Methyl-1-pentene | 5[c] | 2-Methyl-1-pentanol | 100 | 95.0 |
| Cyclopentene | 5[c] | Cyclopentanol | 100 | 95.0 |
| Cyclohexene | 60 & 15[e] | Cyclohexanol | 100 | 98.0 |
| 1-Methylcyclopentene | 60 & 15[e] | trans-2-Methyl-cyclopentanol | >99[f] | 94.0 |

[a]By GC analysis after oxidation.
[b]By GC analysis using an internal standard.
[c]Reactions were over after the addition of the alkenes, but were oxidized after specified time.
[d]Isolated yield.
[e]After 60 min. at room temperature, 15 min. under reflux.
[f] < 1% cis isomer.

EXAMPLE 4

The utility of borane-1,4-thioxane for hydroboration-oxidation is further illustrated by the conversion of (−)-B-pinene to (−)-cis-myrtanol.

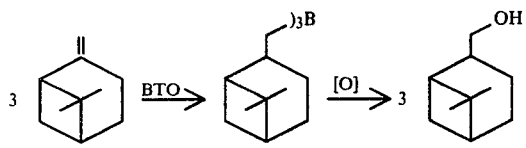

Hydroboration was carried out by adding (−)-B-pinene (11.9 ml, 75 mmol, 95.5% optical purity) dropwise to a well-stirred mixture of borane-1,4-thioxane (3.13 ml, 25 mmol) and pentane (18.3 ml) at room temperature (under nitrogen). The solution was allowed to stand for 15 min. to complete the hydroboration. Then ethanol (15 ml) was added, followed by 3 M sodium hydroxide (25.0 ml, 75 mmol). The reaction mixture was then immersed in a cooling bath and 30% aqueous hydrogen peroxide (9.4 ml, 75 mmol) was added dropwise over 15 min. at such a rate that the temperature did not rise over 35° C. (gentle reflux). The reaction mixture was then heated under reflux for 1 hour and then poured into ice-water (300 ml). The mixture was extracted with ether (70 ml). The ether layer was washed thoroughly with water (3×200 ml), followed by saturated brine solution (50 ml). The organic layer was dried over anhydrous potassium carbonate, filtered, and concentrated. Distillation under vacuum provided pure (−)-cis-myrtanol: 9.0 g, a yield of 79%; b.p. 68°–69° C.

EXAMPLE 5

The possibility of removing the 1,4-thioxane as the sulfoxide with the recovery of the organoborane is illustrated by the following preparation and isolation of tri-n-octylborane.

To a well-stirred solution of borane-1,4-thioxane (3.13 ml, 25 mmol) in tetrahydrofuran (10.0 ml), making the solution 1.0 M in borane, was added (under nitrogen) 1-octene (11.8 ml, 75 mmol) at room temperature. After about 10–15 min., aqueous sodium hypochlorite (3.86 ml, 275 mmol) was then added dropwise over 45 min. at room temperature. Following the addition, the reaction mixture was stirred for 15 min. The aqueous layer was treated with sufficient potassium carbonate to give a separate aqueous phase in which the sulfoxide dissolves. The organic layer was separated under nitrogen. The aqueous layer was washed with 2×8 ml of tetrahydrofuran. The combined extract was dried over anhydrous magnesium sulfate. Filtration yields a solution of tri-n-octylborane in tetrahydrofuran. Removal of solvent yielded tri-n-octylborane; 8.42 g, yield 96%.

The foregoing detailed description has been given for clearness of understanding only, and no unnecessary limitations should be understood therefrom, as modifications will be obvious to those skilled in the art.

What is claimed is:
1. Borane-1,4-thioxane.
2. Borane-1,4-thioxane according to claim 1 which is approximately 8 molar in borane.
3. A process of producing borane-1,4-thioxane which comprises contacting 1,4-thioxane with diborane.
4. A process according to claim 3 in which the reaction is effected at about room temperature.

* * * * *